United States Patent [19]
Chareyre

[11] Patent Number: 5,527,373
[45] Date of Patent: Jun. 18, 1996

[54] PROCESS FOR TREATMENT BY LUMBRICID-COMPOSTING AND DEVICE FOR ITS IMPLEMENTATION

[75] Inventor: André R. Chareyre, La Batie Rolland, France

[73] Assignee: Naturba Inc., Quebec, Canada

[21] Appl. No.: 601,379

[22] Filed: Oct. 23, 1990

[30] Foreign Application Priority Data

Oct. 27, 1989 [FR] France .................................. 89 14616

[51] Int. Cl.⁶ .................................. C05F 9/02; C05F 9/04
[52] U.S. Cl. .......................... 71/9; 435/290.1; 435/290.2; 435/290.4; 71/13; 71/21
[58] Field of Search ................................ 422/184; 71/9, 71/13, 21; 435/290.1, 290.2, 290.4

[56] References Cited

U.S. PATENT DOCUMENTS

| | | | |
|---|---|---|---|
| 4,135,908 | 1/1979 | Widmer | 71/9 |
| 4,139,640 | 2/1979 | Kipp, Jr. | 71/9 X |
| 4,226,832 | 10/1980 | Roumens | 71/9 X |
| 4,236,910 | 12/1980 | Norin et al. | 71/9 |
| 4,285,719 | 8/1981 | Criss | 71/901 X |
| 4,552,726 | 11/1985 | Grappelli et al. | 71/9 X |

FOREIGN PATENT DOCUMENTS

| | | |
|---|---|---|
| 0091495 | 4/1982 | European Pat. Off. . |
| 2364875 | 4/1978 | France . |

*Primary Examiner*—Ferris Lander
*Attorney, Agent, or Firm*—Oliff & Berridge

[57] ABSTRACT

A process includes the steps of: introducing, in a sequential manner and at a predetermined frequency, a substrate of organic waste substances by loading from above inside at least one cylindrical container of circular, polygonal or other cross-section having a vertical axis and at least one transverse horizontal dimension of which is small, in other words of the order of 1 m or even less, the vertical walls of which are at least partially made from a non-gastight material, such as a porous or aerated material; introducing into this pile or windrow lumbricids which will climb upwards; withdrawing, in a sequential manner and at a predetermined frequency, the lower substrate layer of previously lumbricid-composted organic material, this withdrawal causing the substrate to be lowered sequentially, under gravity, at a speed at most equal to that at which the lumbricids climb; and, removing the substrate of previously lumbricid-composted organic material. Such a process can be applied to the field of treating organic urban waste substances.

22 Claims, 3 Drawing Sheets

PROCESS FOR TREATMENT BY LUMBRICID-COMPOSTING AND DEVICE FOR ITS IMPLEMENTATION

BACKROUND OF THE INVENTION

The present invention relates to a process for treatment by lumbricid-composting and a device for its implementation.

In order to obtain a soil ameliorator of the mold or compost type from organic residues originating from urban waste substances or other similar waste substances, it is conventional to make use of lumbricids which ensure that the substances are broken up, aerated and mixed so as to promote the various aerobic fermentations required for their transformation into humus.

DESCRIPTION OF THE PRIOR ART

A treatment process is currently known which consists in placing the lumbricids in a lower layer and in depositing the organic residues in piles or windrows in the form of a plurality of superposed layers. These lumbricids, whilst effecting the breaking up, mixing and aeration of these waste substances, gradually climb towards the top of this windrow. Once they have reached the upper layer, the latter, having been composted, is withdrawn while all those adjacent layers situated beneath are removed and conveyed with a view to storing and packaging them.

The upper layer in which the lumbricids are still situated and which had been taken away beforehand is then deposited again at the base of a new windrow on which a plurality of successive layers of waste substances, in a stratified form, are again stacked, and the cycle begins again.

Now, this type of process has the disadvantage of discontinuous implementation which thus conflicts with a regular addition of fresh organic material to be treated and with the taking away of this organic material which has been lumbricid-composted.

In addition, this process requires an increase in the number of handlings of the upper layer of the windrow, and constant surveillance of the evolution of the migration of the lumbricids inside the windrow in order to be able to perform the operation of taking away the various layers which have been composted as soon as the lumbricids have reached this upper layer.

What is more, the height of the windrows is limited to several decimeters due to the absence of anaerobiosis-generating aeration.

A process is also known, in particular from EP-A-91,495 which consists in accumulating organic waste substances in towers or silos with loading from above and withdrawal from below as the migration of the lumbricids, climbing upwards, progresses. However, this process has the disadvantage of creating considerable thermal accumulations, the organic waste substances being very poor conductors of heat and having a high thermogenesis resulting from the microbial and, possibly, lumbricid biological activity. The removal of the quantities of heat thus generated and the gases resulting from the fermentation, and the oxygen requirements necessitate the provision of complex devices for cooling, for exchanging fluids in the substrate and/or for imparting movements to the latter. Due to the complexity of the means for its implementation and their low efficiency, this process has never been exploited industrially.

SUMMARY OF THE INVENTION

The present invention aims to overcome these disadvantages by providing a process for treatment by lumbricid-composting which takes place continuously and which permits an addition, which is sequential and at a selected frequency, of the residues of organic material to be treated, and a device for its implementation which is simple to construct and to use.

To this end, the process consists:

in introducing, in a sequential manner and at a predetermined frequency, the substrate of organic waste substances by loading from above inside at least one cylindrical container of circular, polygonal of other cross-section, of vertical axis, and at least one transverse horizontal dimension of which is small, in other words of the order of 1 m or even less, and the vertical walls of which are at least partially made from a non-gastight material, such as a porous or aerated material, in introducing into this windrow lumbricids which will climb upwards, in withdrawing, in a sequential manner and at a predetermined frequency, the lower substrate layer of previously lumbricid-composted organic material, this withdrawal causing the substrate to be lowered sequentially, under gravity, at a speed at most equal to that at which the lumbricids climb, and in removing the substrate of previously lumbricid-composted organic material.

By virtue of this process, it is no longer necessary to follow the evolution of the lumbricids inside the substrate of organic material and it is no longer necessary to handle the upper layer of the windrow. Furthermore, the small transverse dimension of each container facilitates the removal of the quantities of heat, and the aerated nature of their vertical walls facilitates the removal of the fermentation gases and the entry of oxygen.

By virtue of the establishment of a predetermined frequency for the loading of the substrate of organic material and the unloading of the previously lumbricid-composted organic material, it is possible, depending on the nature of the organic waste substances constituting this substrate to be treated, to obtain maximum efficiency.

According to a general embodiment of the invention, the device for the implementation of the process comprises a fixed upper frame supporting at least one container open at its upper end and partially closed at its lower end, intended to receive the substrate of organic waste substances to be treated, means for introducing this substrate of organic waste substances into the container in a sequential manner and at a predetermined frequency, means for withdrawing, in a sequential manner, the lower layer of substrate of previously lumbricid-composted organic material, and means for removing this lumbricid-composted and withdrawn substrate.

This device preferably comprises a plurality of containers of a parallelepipedal shape of flattened rectangular cross-section, arranged side by side in a battery.

According to one feature of the invention, the means for introducing the substrate of organic waste substances to be treated consist of a conveyor belt whose downstream end is situated above the upper orifice of each container.

This type of conveyor is particularly well suited as it facilitates, depending on the adjustment of its delivery rate, the introduction, in a sequential manner and at the predetermined frequency, of the substrate of organic material to be treated.

The means for removing the substrate of previously lumbricid-composted and withdrawn organic waste substances advantageoulsy consist of a conveyor belt whose upstream end is situated below the means for withdrawing the lower layer of the substrate of organic material to be treated, in other words below the base of each container.

According to one embodiment of the invention, the vertical walls of the container consist of wire netting or another similar material.

This aerated material, the dimension of whose openings is adapted so as to avoid the lateral loss of organic material to be treated, enables the latter to be well aerated and thus improves its satisfactory decomposition.

According to a first embodiment of this device, the means for withdrawing the lower layer of the substrate of previously lumbricid-composted organic material comprise an upper frame which supports the container and below which is arranged a lower frame supporting a carriage which can move horizontally with a travel at least equal to the length of the base of the container, this carriage supporting mechanical means for scraping the part of the substrate retained by longitudinal bars forming a grid and partially blocking the lower orifice of the container.

The longitudinal bars normally hold the substrate which cannot flow out between them by an arching and packing phenomenon.

For example, the mechanical means for scraping the lower part of the substrate of previously lumbricid-composted organic material consist of the blades of a rotor whose horizontal shaft is supported by the carriage transversely to the fixed frame, these blades being distributed in the same number of sets as the lower orifice of the container has gaps between the longitudinal bars, and each set of blades containing at least one blade, means being provided in order to ensure the driving in rotation of the rotor upon each horizontal travel of the carriage at a speed of rotation such that the linear speed of the free ends of the blades differs from that of the carriage.

The scraping by means of the blades of the rotor eliminates the arching and packing of the waste substances of the substrate of previously lumbricid-composted organic material, the layer directly above being packed, under gravity, onto the longitudinal bars forming a grid.

According to one simple embodiment of the invention, the means for driving the carriage in translation over its longitudinal travel and for driving the rotor in rotation are combined and consist of a pinion keyed at one of the ends of the shaft of its rotor and meshing with a fixed longitudinal rack arranged horizontally along one of the side beams of the fixed upper frame and whose length is at least equal to that of the travel of the carriage, the shaft of the rotor carrying at its other end a second keyed pinion on which is engaged a transmission chain linking this pinion in rotation with the output pinion of a geared motor, the number of teeth of the pinion meshing with the fixed rack being determined so as to obtain the desired difference between the linear speed of the carriage and the rotational speed of the free ends of the blades of the rotor.

The passage frequency of the movable carriage is advantageously 5 weeks and the translational speed is 4.7 meters per minute.

This passage frequency and this speed of advancement depend on the nature of the organic material to be treated, which is favourable for good efficiency of this device.

Given the generally considerable length of the container, the longitudinal bars must be held by intermediate crosspieces whose presence has the disadvantage of forming an obstacle to the descent of part of the lower layer of the substrate of previously lumbricid-composted organic material.

In order to eliminate this disadvantage, according to an advantageous embodiment of the invention, on the one hand, each intermediate crosspiece supported by the side beams of the fixed frame, of circular cross-section, is mounted pivotably about its longitudinal axis which is parallel to that of the shaft of the rotor and, on the other hand, it carries, in at least one of the gaps between the bars and in the same vertical plane as the corresponding set of blades of the rotor of the carriage, a set of radial ribs of a dimension such that the free end of at least one of them is situated on the trajectory of the blades of the abovementioned set of blades so as to be activated by one of them when the carriage passes by and so as to cause consequently a rotation, over a fraction of a revolution, of the crosspiece in question.

Evidently, as a result the substrate of previously lumbricid-composted organic material, possibly retained on these crosspieces, falls, which prevents the formation of agglomerates or non-scraped zones.

Each blade of the rotor advantageously has a shearing bolt capable of fracturing under the influence of a force of 500 kg and more.

It enables the blades to be protected in the event of locking.

According to an advantageous form of this first alternative embodiment of the invention, which aims to permit a single carriage to be used beneath various containers, arranged side by side, the lower frame supporting the carriage is mounted so as to be displaceable transversely beneath all these containers.

For example, the lower frame of the same length as the fixed upper frame comprises a guide slideway carried by two end plates, each of which is supported by two running rollers permitting displacement beneath all of the containers arranged side by side, it being possible for motor means to be provided in order to control each transverse displacement of this lower frame from one end container to the other.

According to an alternative embodiment of the invention, the longitudinal bars which partially close the lower orifice of the container consist of cylindrical rods mounted pivotably about their longitudinal axis at the level of the lower orifice of the container in question, motive means being provided in order to enable them to be driven in rotation, in a sequential manner and at a predetermined frequency, via chains or belts and pinions, and the means, underneath, for scraping the lower layer of substrate of previously lumbricid-composted organic material consist of radial fins carried by each longitudinal rod, each of them carrying at least one fin.

In order to prevent any undesired rotation of the longitudinal bars and of their fins, according to a simple embodiment of this second embodiment of the invention, a horizontal rack is provided, carried by vertical slideways integral with the fixed frame, so as to be able to be displaced between a retracted position and a locked position in which it meshes with the pinions keyed at one of the ends of the longitudinal bars.

BRIEF DESCRIPTION OF THE DRAWING

The invention will, in any case, be better understood with the aid of the description below, made with reference to the attached diagrammatic drawing showing by way of non-limiting example two embodiments of the device for implementing the lumbricid-composting process according to the invention.

DESCRIPTION OF THE PREFERRED EMBODIMENTS

Figure 1:
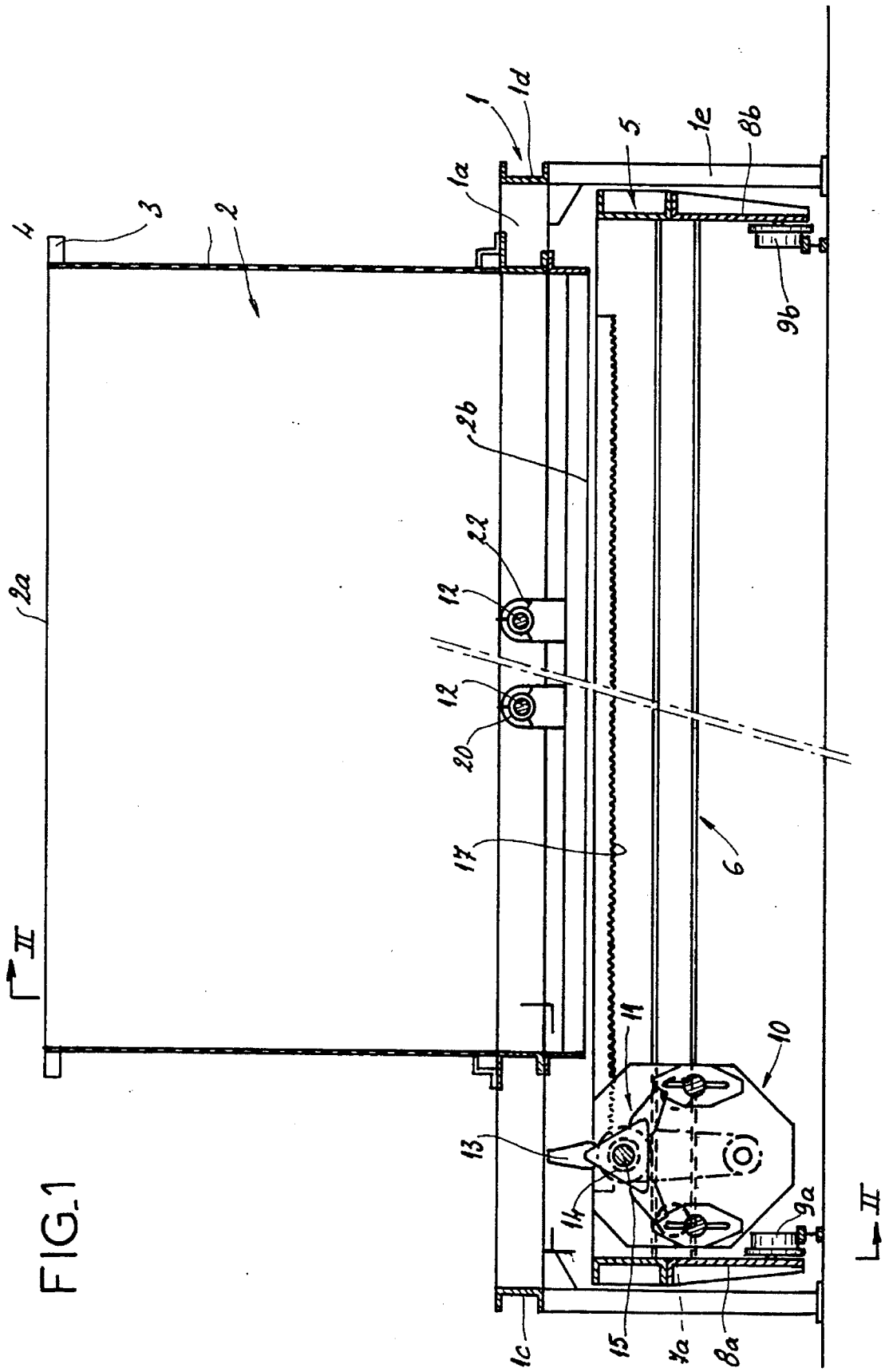
FIG. 1 is a view in section of the device along the line I—I in FIG. 2.
Figure 2:
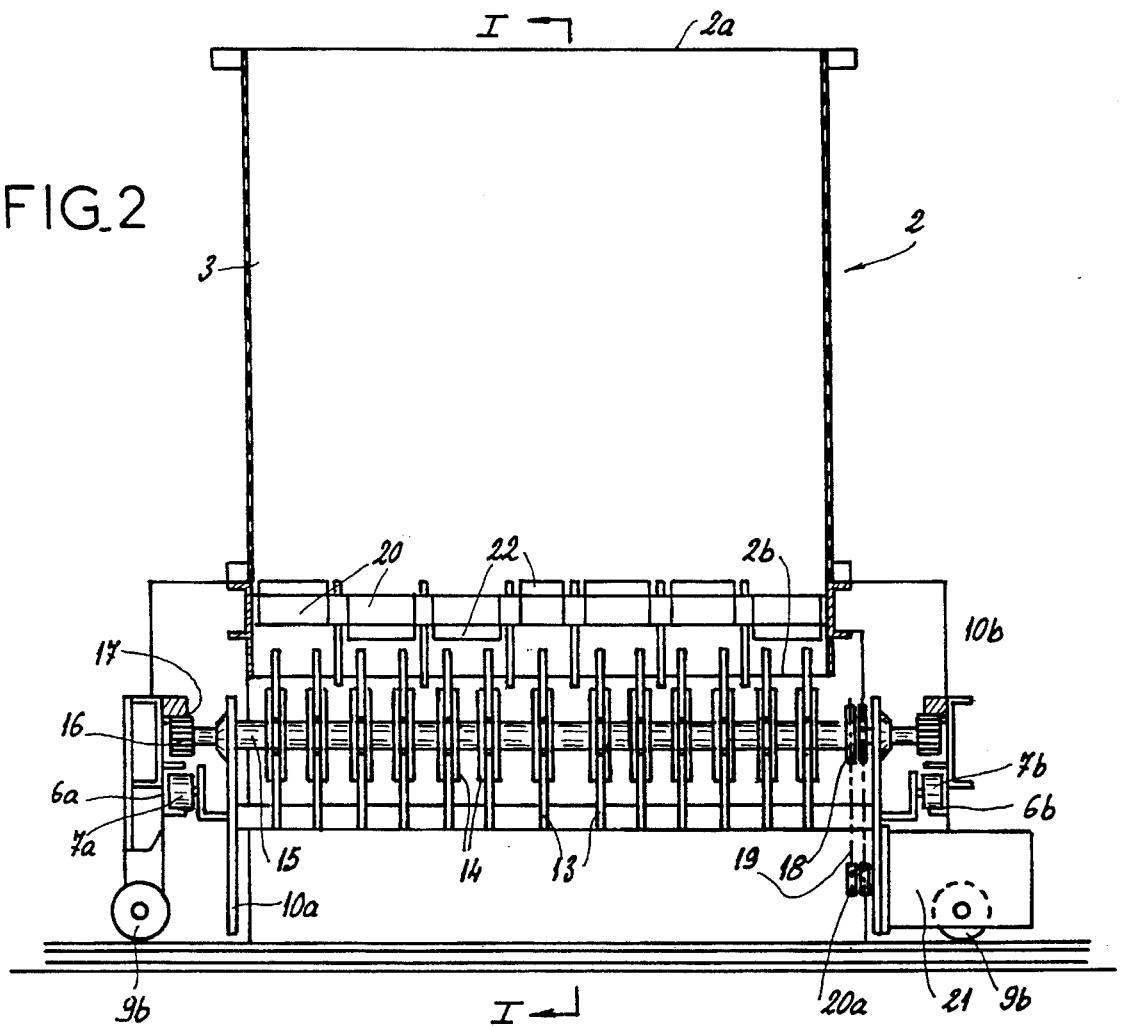
FIG. 2 is a view in section of the device along the line II—II in FIG. 1.

The first embodiment of the device according to the invention, as shown in FIGS. 1 and 2, comprises a fixed frame 1 consisting of two side beams 1a and 1b, and two crosspieces 1c, 1d arranged parallel to one another and perpendicularly to the side beams. This frame is raised relative to the surface of the ground by means of feet 1e.

This frame supports a container 2, of parallelepipedal shape, open at its upper end 2a and partially blocked at its lower end 2b. This container 2 is intended to receive the substrate of organic material to be treated, through its upper orifice 2a, in a sequential manner and at a previously determined frequency, and to contain the lumbricids.

The vertical walls 3 of this container 2 are made from an aerated material such as wire netting. They are surmounted, at their upper ends, by a reinforcing rim 4 and are fixed, at their lower ends, by appropriate mechanical means, on the side beams and the crosspieces of the fixed upper frame 1.

Beneath the base of the container 2 is arranged a movable lower frame 5, of the same length as the upper fixed frame 1 and comprising a guide slideway 6 consisting of two parallel rails 6a, 6b. This slideway is carried by two end plates 8a, 8b, each of which is supported by two running rollers, 9a, 9b respectively. These rollers enable this movable frame 5 to move translationally beneath various containers 12 arranged in a battery, side by side, so as to increase the surface area to be scraped. This translational movement can be effected manually or via a drive means, such as an electric motor, not shown in the drawing.

A carriage 10 is mounted on the guide slideway 6. This carriage can therefore move horizontally in a direction perpendicular to that of the movable lower frame 5, with a travel at least equal to that of the base of the container 2, and one end position of which is shown in FIG. 1. This horizontal translational movement of the carriage 10 takes place via running rollers 7a, 7b carried by lateral end plates 10a, 10b of the carriage 10.

The carriage 10 supports mechanical means 11 for scraping that part of the substrate of previously lumbricid-composted organic material situated below the lower orifice 2b of the container 2, partially blocked by longitudinal bars 12.

The mechanical means 11 for scraping this lower part of the substrate of previously lumbricid-composted organic material consist of the blades 13 of a rotor 14 whose horizontal shaft 15 is supported by the carriage 10, transversely to the fixed frame 1. These blades 13 are distributed in the same number of sets as the lower orifice 2a of the container 2 has gaps between longitudinal bars 12. Each set of blades comprises three blades 13 arranged at 120° to one another, as is shown better in FIG. 3. Each of these blades 3 is locked on its shaft by a safety bolt 13a intended to fracture when the blade 13 in question is subjected to a tangential force of the order of 500 kg. The presence of this bolt prevents the blade from fracturing in the event of locking.

The means for driving the carriage 10 in translational movement over its longitudinal travel and for driving the rotor 14 in rotation are combined and consist, one the one hand, of a pinion 16 keyed at one of the ends of the shaft of its rotor 14, this pinion 16 meshing with a fixed longitudinal rack 17 arranged horizontally along one of the side beams of the fixed upper frame 1 and, on the other hand, of an output pinion 21a of a geared motor 21 linked in rotation to a third pinion 18, keyed on the other end of the shaft 15 of the rotor.

The length of this rack 17 is, of course, at least equal to that of the travel in horizontal translational movement of the movable carriage 10 so as to permit it to be driven over this entire length.

The number of teeth of the pinion 16 meshing with the fixed rack 17 is determined so as to obtain a difference in speed between the linear speed of the carriage 10 and the free rotational speed of the blades 13 of the rotor. The longitudinal bars 12, held by intermediate crosspieces 20, are uniformly distributed beneath the base of the container 2 at the level of its lower orifice 2b.

Figure 3:
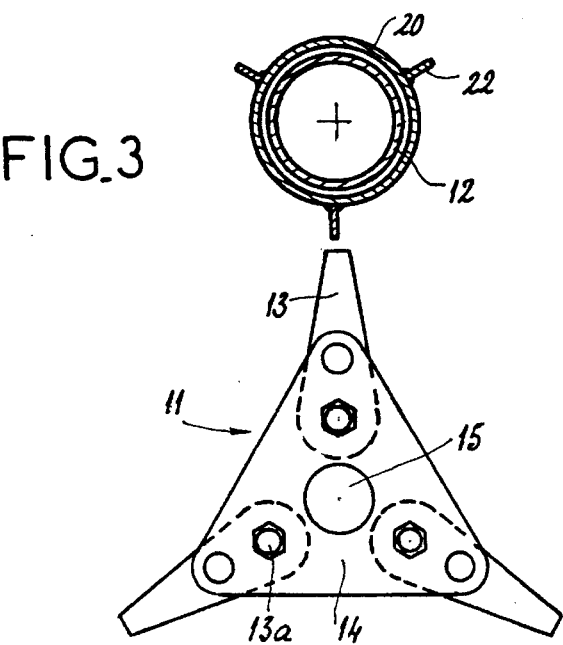
FIG. 3 is a view in cross-section, on a larger scale, of a set of blades of the rotor and of a longitudinal rod.

These crosspieces 20 have the disadvantage of forming an obstacle to the descent of the lower part of the layer of the substrate of previously lumbricid-composted organic material. In order to eliminate this disadvantage, each crosspiece 20 supported by the side beams 1a, 1b of the fixed frame 1, of circular cross-section, is mounted pivotably about its longitudinal axis which is parallel to that of the shaft 15 of the rotor 14, and carries, in the gaps between bars 12 and in the same vertical plane as the set of blades 13, a set of radial ribs 22. Each set of ribs 22, as shown in FIG. 3, consists of three ribs 22 arranged at 120° to one another. These ribs 22 have a dimension such that the end of at least one of them is situated on the trajectory of the corresponding set of blades 13 in order to be able to be activated by one of the blades, when the carriage 10 passes, and to cause, consequently, a rotation of the crosspiece in question, over a fraction of a revolution. As a result, the substrate of previously lumbricid-composted organic material which is retained on these crosspieces 20 falls.

Figure 4:
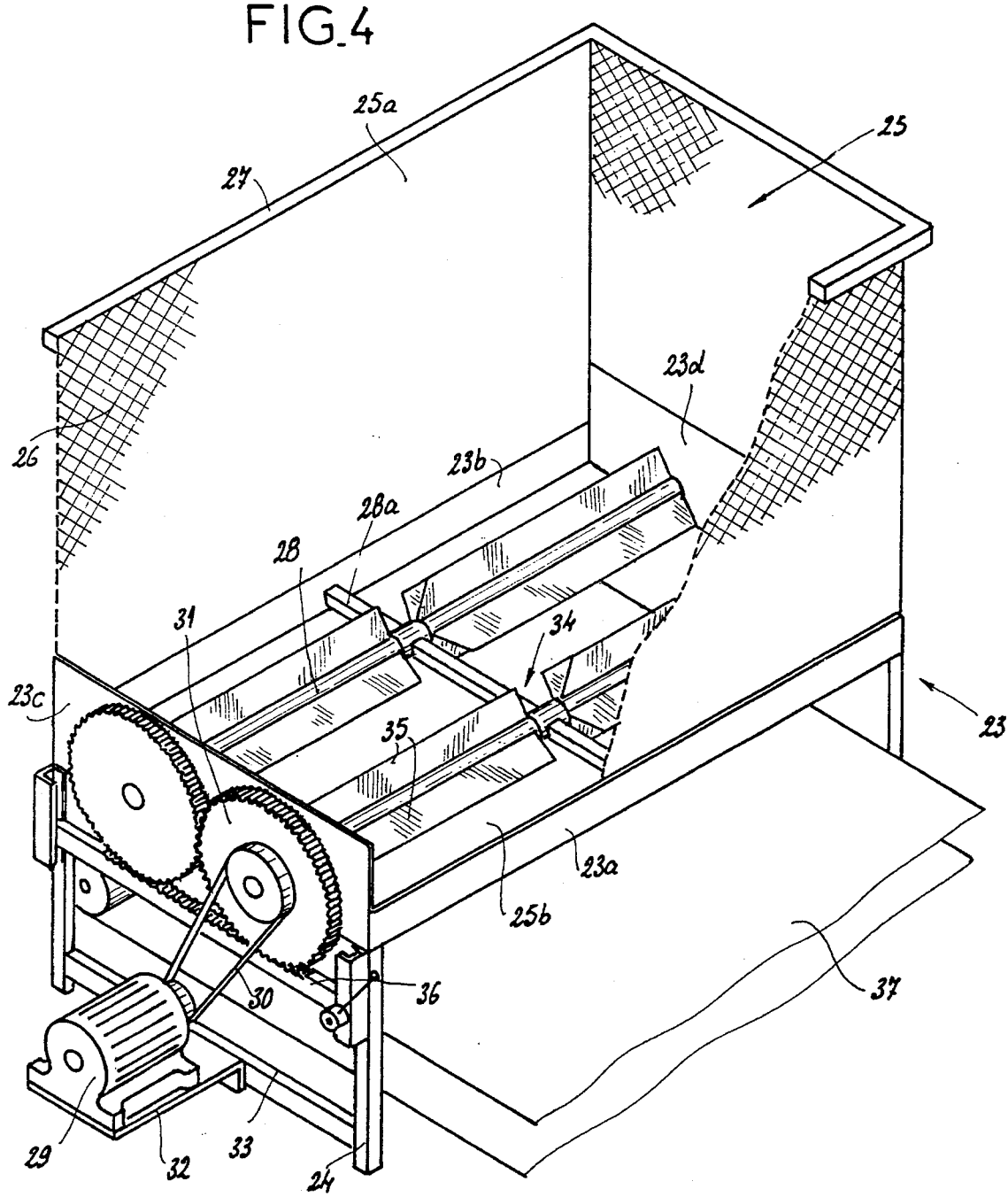
FIG. 4 is a view in perspective of a second embodiment of the device.

The second embodiment of this device is shown more particularly in FIG. 4.

This device comprises a fixed frame 23 consisting of two side beams 23a and 23b and two lateral edge plates 23c, 23d serving as crosspieces. Each of these plates has a sufficient height to enable it to support drive means. This frame 23 is raised relative to the ground by means of feet 24. It supports a container 25 of parallelepipedal shape, open at its upper end 25a, and partially blocked at its lower end 25b. This container 25 is intended to receive, through its upper orifice, the substrate of organic materials to be treated by lumbricids, in a sequential manner and at a predetermined frequency.

The vertical walls 26 of the container 25 are made from an aerated material such as wire netting. They are surmounted, at their upper ends, by a protective rim 27 and are fastened, at their lower ends, to the side beams 23a, 23b and to the lateral edge plates 23c, 23d.

Longitudinal rods 28, which partially close the lower orifice 25b of the container, are mounted pivotably about their longitudinal axis. Due to the considerable length of the container 25, these rods 28 are supported, in their mid part, by crosspieces 28a which are themselves supported by the side beams 23a, 23b and are arranged perpendicularly to the axis of rotation of the rods 28.

A motor 29 is carried by a plate 32 fixed to a crosspiece 33 of the fixed frame 23. This motor 29 is intended to drive one of the two rods 28 partially closing the lower orifice of the container 25 and each of which supports the mechanical scraping means 34 consisting of four radial fins 35 arranged at 90° to one another. To this end, a pulley 29a, keyed on its output shaft, is linked in rotation, by a belt 30, to a pulley 31a keyed on one of the rods 28, the linking in rotation between the two rods 28 of a same container being ensured by two pinions 31 keyed on the rods and meshing with one another.

So as to prevent any undesired rotation of the longitudinal bars 28, a horizontally displaceable rack 36 is arranged beneath the pinions 31 so as to be able to be displaced between a retracted position and a locked position in which it meshes with the pinions 31.

A conveyor belt 37, arranged beneath the base of the container 25 and whose upstream end is situated beneath the scraping means, enables the substrate of previously lumbricid-composted and withdrawn organic material to be removed.

The lumbricid-composting process takes place as described below:

The substrate of waste substances of organic material to be treated is introduced in a sequential manner and at a predetermined frequency by loading from above at the level of the upper orifice 2a, 25a of a container 2, 25 by way of mechanical introducing means such as a conveyor belt, not shown on the drawing and the downstream end of which is situated on the upper end of the container.

The lumbricids are introduced into the windrow and subsequently perform their work of aerating and transforming the substrate as they climb.

The lower layer of substrate of previously lumbricid-composted organic waste substances is withdrawn in a sequential manner and at a predetermined frequency. This withdrawal is effected, in the first embodiment of the device, by mechanical scraping means 11 consisting of the blades 13 of a rotor 14 whose horizontal shaft 15 is supported by the carriage 10 transversely to the fixed frame 1. These blades 13 are distributed in the same number of sets of blades as the lower orifice 2b of the container 2 has gaps between the longitudinal bars 12 so as to permit, by way of their rotation accompanied by the translational movement of the carriage 10 beneath the base of the container 2, extraction of the lower layer of the substrate of waste substances of previously lumbricid-composted organic material.

The previously lumbricid-composted organic material which is retained on the crosspieces 20 is for its part driven by the rotation, by a fraction of a revolution, of these pivotably mounted crosspieces, occasioned by the contact between the ribs 22 arranged regularly at the periphery of the crosspieces 20 and one of the blades 13 of the rotor 14.

The withdrawal of the substrate of previously lumbricid-composted organic waste substances takes place in a sequential manner and at a predetermined frequency, in the other embodiment of the device, by way of the mechanical means 34 consisting of the four radial fins 35 arranged at 90° to one another and placed on the rods 28 driven in rotation by the motor 29 and partially blocking the lower orifice of the container 25.

The removal of the substrate of waste substances of previously lumbricid-composted and withdrawn organic material is performed via a mechanical means such as a conveyor belt whose upstream end is situated beneath the mechanical scraping means, in other words beneath the container.

I claim:

1. A process for treating organic material by lumbricid-composting, comprising the steps of:

introducing organic material into at least one tubular container in a sequential manner and at an introduction rate by loading the organic material from above, the at least one tubular container having a vertical axis, and at least one transverse horizontal dimension of approximately 1 m or less, said at least one tubular container having vertical walls substantially made from a non-gastight material, and said tubular container lacking mechanical mixing means therein;

introducing into said at least one tubular container lumbricides which will climb upwards while composting the organic waste, said lumbricids climbing at a lumbricid climbing rate;

withdrawing continuously, in a sequential manner and at substantially said introduction rate, a lower layer of lumbricid-composted organic material, said withdrawing causing the organic material to be lowered sequentially at a rate of at most equal to said lumbricid climbing rate; and removing the lumbricid-composted organic material.

2. The process of claim 1, wherein the tubular container is of circular or polygonal cross section.

3. The process of claim 1, wherein in the step of withdrawing, the organic material is lowered sequentially under gravity.

4. The process of claim 1, wherein the non-gastight material is a porous or aerated material.

5. A device for treating organic material by lumbricid-composting, comprising:

an upper frame supporting at least one container open at its upper end and partially closed at its lower end, said container for receiving organic material to be composted having a vertical axis, at least one transverse horizontal dimension of approximately 1 m or less, and vertical walls substantially made from non-gastight material, and said container lacking mechanical mixing means therein;

means for introducing the organic material into said at least one container in a sequential manner and at a rate;

means for continuously withdrawing, in a sequential manner, a lower layer of lumbricid-composted organic material and thus causing the organic material to descend at substantially said rate during lumbricid-composting, said rate being at most equal to a lumbricid climbing rate.

6. The device as claimed in claim 5, wherein said at least one container comprises a plurality of containers.

7. The device as claimed in claim 6, wherein said plurality of containers are of a parallelepipedal shape of flattened rectangular cross-section, arranged side by side in a battery.

8. The device as claimed in claim 5, wherein the means for introducing the organic material to be treated is comprised of a conveyor belt having a downstream end situated above the upper opening of said at least one container.

9. The device as claimed in claim 5, wherein the means for removing the lumbricid-composted organic material comprises a conveyor belt having an upstream end situated below the means for withdrawing the lower layer of the lumbricid-composted organic material.

10. The device as claimed in claim 5, wherein the non-gastight material of the vertical walls of said at least one container is wire netting.

11. The device as claimed in claim 5, wherein the means for withdrawing the lower layer of the lumbricid-composted organic material comprises the upper frame which is fixed and supports said at least one container and a lower frame arranged below the upper frame and supporting a carriage horizontally movable over a length at least equal to the length of the base of the container, said carriage supporting mechanical means for scraping the organic material retained above the lower opening of the container by longitudinal bars forming a grid.

12. The device as claimed in claim 11, wherein the longitudinal bars forming a grid at the bottom of each container are held by intermediate crosspieces.

13. The device as claimed in claim 12, wherein each of said intermediate crosspieces is supported by the side beams of the fixed frame, is of circular cross-section, and is mounted pivotably about its longitudinal axis which is parallel to that of the horizontal shaft of the rotor, and wherein each of said intermediate crosspieces carries a set of radial ribs in at least one of the gaps between the bars forming a grid and in the same vertical plane as the corresponding set of blades of the rotor of the carriage, said set of radial ribs having a dimension such that the free end of at least one of said set of radial ribs is situated on the trajectory of the blades of the set of blades so as to be activated by one of the blades when the carriage passes by, thus causing a rotation, over a fraction of a revolution, of the corresponding crosspiece.

14. The device as claimed in claim 13, wherein each blade of the rotor has a shearing bolt capable of breaking when said bolt is subjected to a force of the order of 500 kg or more.

15. The device as claimed in claim 11, wherein the mechanical means for scraping the lumbricid-composted organic material comprises a rotor having blades and a horizontal shaft supported by the carriage transversely to the fixed frame, said blades being distributed in the same number of sets as the number of gaps between the longitudinal bars, and each set of blades comprising at least one blade, and said device further comprising an ensuring means for ensuring that the driving in rotation of the rotor upon each horizontal travel of the carriage is at a speed of rotation such that the linear speed of the free ends of the blades differs from that of the carriage.

16. The device as claimed in claim 15, wherein the ensuring means comprises means for driving the carriage in translation in a longitudinal direction and means for driving the rotor in rotation, wherein a first pinion is keyed at one of the ends of the horizontal shaft of the rotor, the first pinion meshing with a fixed longitudinal rack arranged horizontally along a side beam of the fixed upper frame, the rack having a length which is at least equal to that of the length of travel of the carriage, the horizontal shaft of the rotor carrying at its other end a second keyed pinion on which is engaged a transmission chain linking said second keyed pinion in rotation with an output pinion of a geared motor, and wherein the number of teeth of the first pinion is determined so as to obtain the desired difference between the linear speed of the carriage and the rotational speed of the free ends of the blades of the rotor.

17. The device as claimed in claim 11, wherein said at least one container comprises a plurality of containers and the lower frame is of the same length as the fixed upper frame and comprises a guide slideway carried by two end plates, each of which is supported by two running rollers permitting displacement, and wherein said device further comprises motor means beneath said plurality of containers arranged side by side, said motor means being provided in order to control each transverse displacement of the lower frame from one end container to the other.

18. The device as claimed in claim 11, wherein said at least one container comprises a plurality of containers and the lower frame is of the same length as the fixed upper frame and comprises a guide slideway carried by two end plates, each of which is supported by two running rollers permitting displacement, and wherein said device further comprises motor means beneath said plurality of containers arranged side by side, said motor means being provided in order to control each transverse displacement of the lower frame from one end container to the other.

19. The device as claimed in claim 5, wherein said at least one container has longitudinal bars arranged at its lower end that partially block the lower end of said at least one container, said bars comprising cylindrical rods mounted pivotably about their longitudinal axis at the level of the lower end of the at least one container, each rod carrying at least one radial fin, and wherein a motor means is provided in order to enable said bars to be driven in rotation, in a sequential manner and at a desired frequency, via chains or belts and pinions, for scraping the lower layer of lumbricid-composted organic material.

20. The device as claimed in claim 19, wherein said at least one container further comprises a lower frame arranged below the upper frame, the lower frame supporting the longitudinal bars, and further comprising a horizontal rack carried by vertical slideways integral with the lower frame so as to be able to be displaced between a retracted position and a locked position in which the horizontal rack meshes with the pinions keyed at one of the ends of the rods.

21. The device as claimed in claim 5, wherein the non-gastight material is a porous or aerated material.

22. The device as claimed in claim 5, wherein said at least one container has a circular or polygonal cross-section.

* * * * *